United States Patent
Trezza, II et al.

(10) Patent No.: US 7,299,605 B2
(45) Date of Patent: Nov. 27, 2007

(54) ANTI-CURLING FOIL MANUFACTURING PROCESS

(75) Inventors: Michael J. Trezza, II, Pittstown, NJ (US); David A. Szabo, Branchburg, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 10/894,167

(22) Filed: Jul. 19, 2004

(65) Prior Publication Data

US 2006/0010841 A1  Jan. 19, 2006

(51) Int. Cl.
*B65B 47/00* (2006.01)
*B65B 47/08* (2006.01)

(52) U.S. Cl. ............... 53/453; 53/559; 53/140

(58) Field of Classification Search .......... 53/453, 53/559, 140
See application file for complete search history.

(56) References Cited

U.S. PATENT DOCUMENTS

| | | | | |
|---|---|---|---|---|
| 2,792,593 A * | 5/1957 | Hardgrove, Jr. | ............. | 425/525 |
| 2,900,258 A * | 8/1959 | Wagner | ............. | 53/453 |
| 3,301,393 A * | 1/1967 | Regan, Jr. et al. | ............. | 206/409 |
| 3,341,644 A * | 9/1967 | Allen | ............. | 264/550 |
| 3,353,325 A * | 11/1967 | Jensen et al. | ............. | 53/453 |
| 3,353,329 A * | 11/1967 | Cloud et al. | ............. | 53/453 |
| 3,487,139 A * | 12/1969 | Ayala et al. | ............. | 264/132 |
| 3,545,608 A * | 12/1970 | Berger | ............. | 206/63.3 |
| 3,582,388 A * | 6/1971 | Stayner | ............. | 428/325 |
| 3,766,186 A * | 10/1973 | Mach et al. | ............. | 264/269 |
| 4,424,898 A * | 1/1984 | Thyen et al. | ............. | 206/63.3 |
| 5,228,565 A * | 7/1993 | Sinn | ............. | 206/63.3 |
| 5,341,922 A | 8/1994 | Cerwin et al. | | |
| 5,575,382 A * | 11/1996 | Sobel et al. | ............. | 206/63.3 |
| 5,623,810 A | 4/1997 | Dey et al. | | |
| 5,709,067 A | 1/1998 | Dey et al. | | |
| 5,732,529 A | 3/1998 | Dey et al. | | |
| 5,788,062 A | 8/1998 | Cerwin et al. | | |
| 5,833,055 A | 11/1998 | Cerwin et al. | | |
| 5,868,244 A | 2/1999 | Ivanov et al. | | |
| 5,947,278 A * | 9/1999 | Sawhney et al. | ............. | 206/216 |
| 5,987,855 A | 11/1999 | Dey et al. | | |
| 6,021,625 A | 2/2000 | Cerwin et al. | | |
| 6,047,815 A | 4/2000 | Cerwin et al. | | |
| 6,097,427 A | 8/2000 | Dey et al. | | |
| 6,098,796 A | 8/2000 | Januzeli et al. | | |
| 6,135,272 A | 10/2000 | Sobel et al. | | |
| 6,378,274 B1 * | 4/2002 | Harbour | ............. | 53/453 |
| 6,588,180 B2 * | 7/2003 | Heath et al. | ............. | 53/440 |
| 6,670,028 B2 * | 12/2003 | Ellison et al. | ............. | 428/300.7 |

\* cited by examiner

*Primary Examiner*—Stephen F. Gerrity
(74) *Attorney, Agent, or Firm*—Emil Richard Skula

(57) ABSTRACT

A process for manufacturing a foil package from foil laminate sheet stock. The foil laminate has a top foil sheet and a bottom polymeric sheet laminated to the foil sheet. A cavity is molded into the bottom foil sheet, wherein the cavity has a bottom, a depth and a periphery, such that all of the periphery is substantially arcuate at any horizontal cross-section along the depth of the cavity. The top planar sheet is heat sealed to the bottom molded sheet. The molding process substantially reduces or eliminates curling.

9 Claims, 8 Drawing Sheets

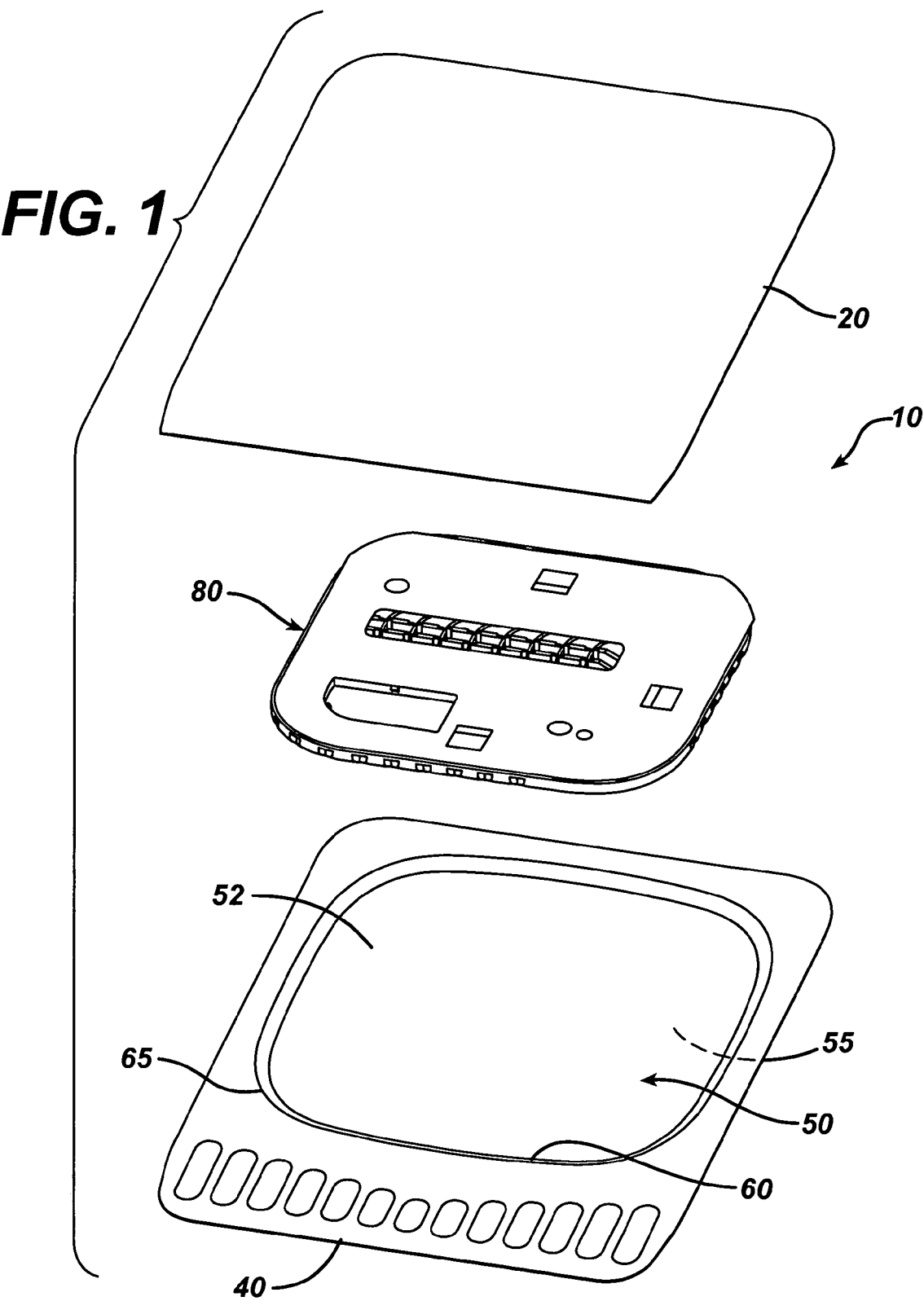

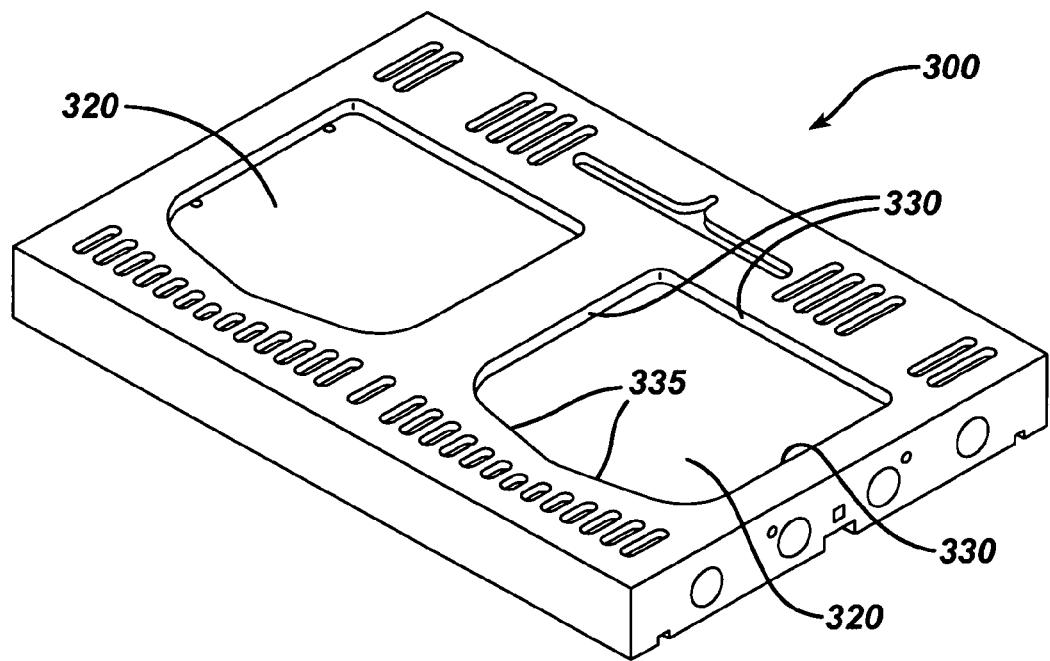
FIG. 4A <u>PRIOR ART</u>

ANTI-CURLING FOIL MANUFACTURING PROCESS

TECHNICAL FIELD

The field to which this invention relates is packaging, specifically the manufacture of foil packages for suture products.

BACKGROUND OF THE INVENTION

The use and manufacture of foil packages is well known in the art. Foil packages are especially useful for sterile medical devices. It is known, for example, to package surgical needles and sutures in foil packages. Foil packages have the advantage of providing a gas-tight, hermetic seal, and the packages provide an impenetrable barrier to pathogens and contaminants. Foil may also be molded to the shape of the device or device package. Foil packages are typically required for medical devices that are moisture sensitive such as bioabsorbable and bioresorbable implantable devices.

Surgical sutures are typically packaged in dispenser packages that protect the suture and any attached needle(s) from damage during handling. Examples of dispenser packages for sutures are contained in U.S. Pat. Nos. 6,135,272, 6,047,815, 6,098,796 and 5,788,062, which are incorporated by reference. The dispenser package must then be inserted into a package providing a sterile barrier. In the case of a moisture sensitive device, the packaging must be gas tight as well. Foil packages for suture dispenser packages, and methods of packaging dispenser packages in outer foil pouches or packages are known in this art. Examples of outer foil packages and methods of forming such foil packages are contained in U.S. Pat. Nos. 6,021,625, 5,987,855, 5,868,244, 5,732,529, 6,097,427, 5,833,055, 5,623,810, 5,709,067 and 5,341,922, which are incorporated by reference.

A typical foil used in manufacturing foil packages is a laminate consisting of an outer polymeric film or sheet, a foil sheet and an inner polymeric film or sheet. The inner polymeric sheet is heat sensitive and can be heated at relatively low temperatures to form a heat seal with an opposed polymeric sheet of another foil. In a typical foil packaging operation, foil from rolls is fed into manufacturing apparatuses. One foil sheet is fed as the upper barrier of the package, while a second foil sheet is roll fed for use in forming the bottom sheet of the package. The sheets are arranged so that the inner polymeric sheets are opposed in order to form the interior of the package. Typically, the machinery will mold a cavity in the bottom sheet, while the top sheet is maintained as planar. After a suture dispenser package is placed in the cavity, the top and bottom foils are cut, and a partial heat seal is formed about the periphery of the package. An opening is typically left to provide for the flow of sterilant gases into the foil package. Once sterilization is complete, the opening in the package is heat sealed, thereby providing a sterile barrier. Another known method of sterilization with foil packages provides for the sealing of the periphery of the package, wherein a vent having a bio-barrier is contained in the package. Typically, two or more packages are connected to the bio-barrier vent via a manifold, and the packages are sealed except for the manifold connection. After sterilization, the manifolds are sealed and the packages are cut apart from each other and the bio-barrier vent.

While the known processes for manufacturing foil packages having molded cavities are acceptable when using foil laminate fed from rolls, there can be problems when attempting to use pre-cut sheets of laminate foil. Specifically, it is known that the laminate foil can exhibit substantial curling after the cavities are molded into the foil sheet. Such curling may interfere with the heat-sealing of a planar laminate foil top to the molded bottom laminate, thereby potentially compromising the integrity of the hermetic seal of the foil package.

Accordingly, there is a need in this art for a novel process for manufacturing foil packages with molded cavities from foil laminate sheets that prevents or substantially reduces curling.

SUMMARY OF THE INVENTION

Therefore, a novel anti-curling process for manufacturing a molded foil outer package from laminate foil sheet is disclosed. In this process a planar foil laminate top sheet and an opposed foil laminate bottom sheet are provided. Each foil laminate sheet has a top polymeric sheet, an inner foil sheet, and a bottom polymeric sheet. The laminate sheets are oriented such that the bottom polymeric sheets of the foil laminates are opposed and facing each other. A mold having a mold cavity is provided. The mold cavity has a periphery and a depth. The periphery is substantially curved or arcuate at any horizontal cross-section section take along the depth of the mold cavity. A package cavity is molded in the bottom sheet such that the package cavity has a periphery and a depth, the package cavity being surrounded by walls and a bottom, wherein the periphery of the package cavity is substantially curved or arcuate at any horizontal cross-section along the depth of the package cavity. The top sheet is mounted to the bottom sheet and a seal is formed such that the cavity in the bottom sheet is enclosed and sealed.

These and other aspects and advantages of the process of the present invention will be more apparent from the following description and accompanying drawings.

BRIEF DESCRIPTION OF THE DRAWINGS

FIG. 1 is an exploded perspective view of a foil package manufactured by the process of the present invention illustrating the top planer sheet, the bottom sheet having a molded cavity, and a dispenser package containing a surgical needle and attached suture.

FIG. 4A is a perspective view of a mold of the prior art having substantially linear sides.

DETAILED DESCRIPTION OF THE INVENTION

Figure 2A:
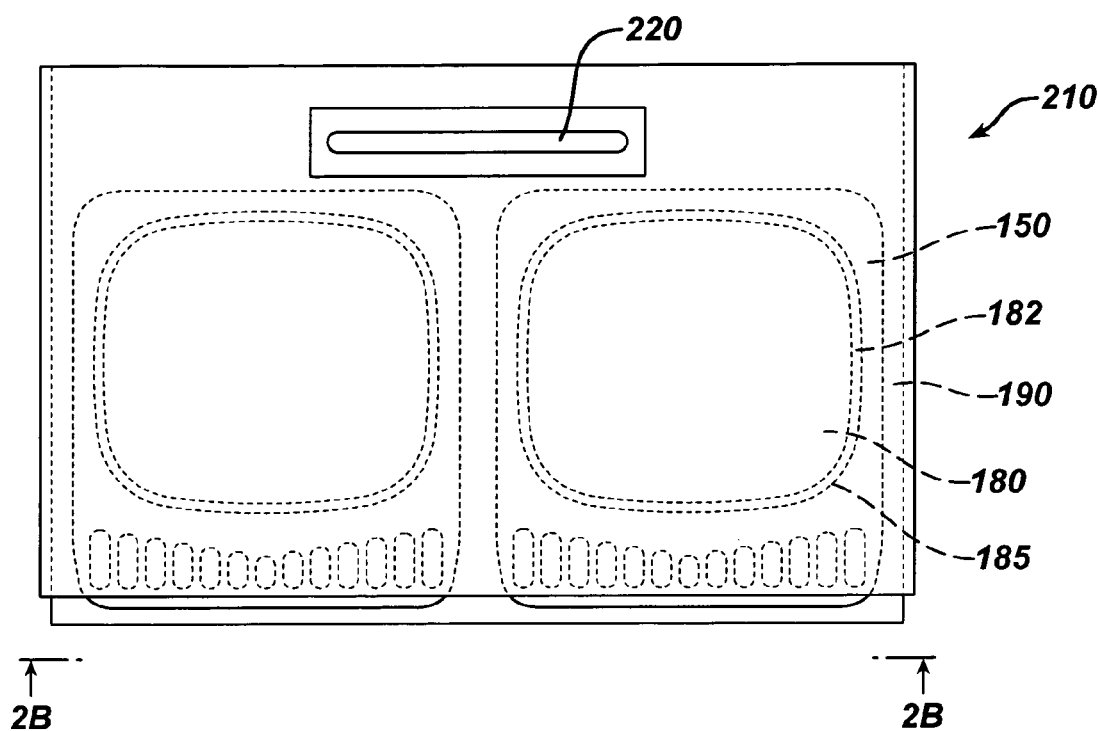
FIG. 2A is a top view of a two strip layout of a package manufactured by the process of the present invention showing a sterilant vent at the top of the strip, prior to cutting the strip into to individual packages.

The foil laminates useful in the practice of the present invention will be conventional, commercially available laminates consisting of an inner metal layer with a top polymer film layer and a bottom polymer film layer. The films may be sheets or coatings. The metal will typically be malleable and commercially available such as aluminum foil. The metal will have a thickness of sufficiently effective to provide a gaseous barrier and permit molding or forming, for example, 40 microns to 51 microns. The bottom polymer film will typically be made from conventional biocompatible marterials such as polyethylene and PET and equivalents thereof. The top polymer film may be made from the afore-mentioned polymers and may also include polyurethanes. It will have a sufficient thickness to provide a moisture barrier and allow for sealing of a seal about the periphery such as a heat seal or ultrasonic seal. The polymer films are bonded to the metal layer by conventional processes. Conventional coating adhesives such as polyurethane adhesives may be used.

A molded package made by the process of the present invention is seen in FIG. 1. The package 10 is seen to have top foil laminate strip 20 and bottom foil laminate strip 40. Molded into the bottom laminate is the package cavity 50. Cavity 50 is seen to have open top 52 and bottom 55 and a depth. The cavity 50 is also seen to have curved or arcuate side walls 60 with rounded corners 65 such that the periphery of the cavity 50 has joined sides all of which are curved or arcuate. The periphery of the package cavity 50 at any horizontal section along the depth is arcuate, i.e., the segments are arcuate or curved. Contained in the cavity 50 of package 10 is the surgical needle and suture package 80.

The molding process useful in the present invention is any conventional molding process using a female mold with a cavity. For example a mating male mold may be used to press and form the laminate in the cavity of the female mold. It is particularly preferred to use a process as illustrated in FIG. 5 wherein a female mold is used, and rather than a male mold, a jet of compressed air is directed against a sheet of laminate to form a package cavity in the foil laminate in the mold cavity of the female mold.

Figure 3A:
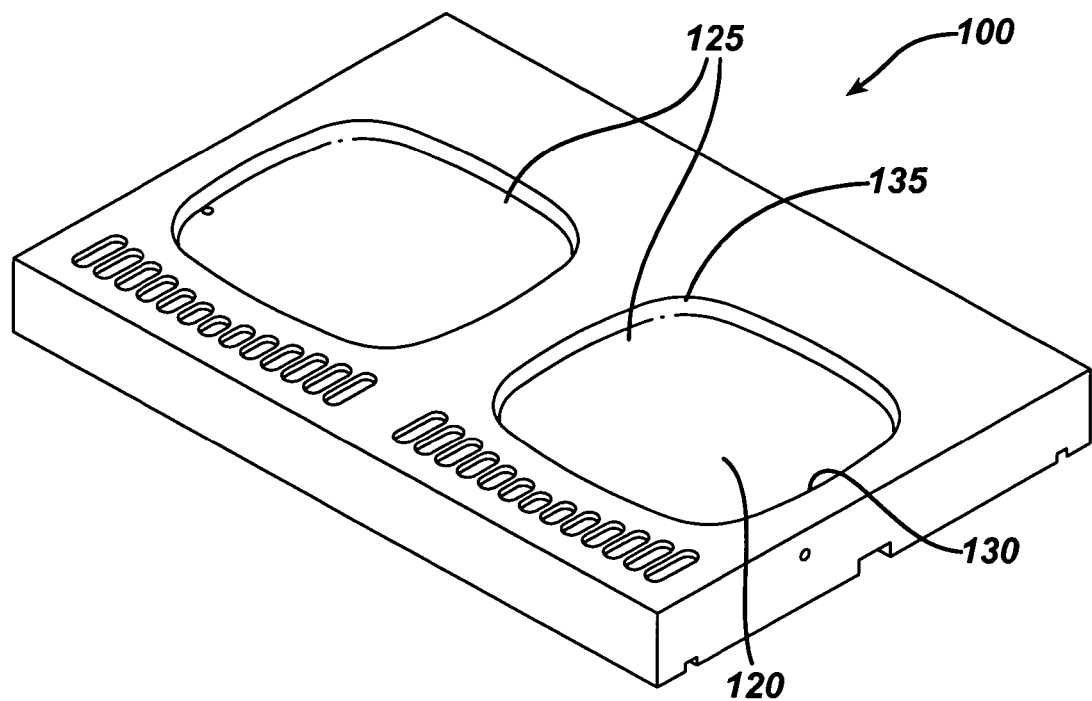
FIG. 3A is a perspective view of a mold useful in the process of the present invention with a mold cavity having a curved periphery.
Figure 5:
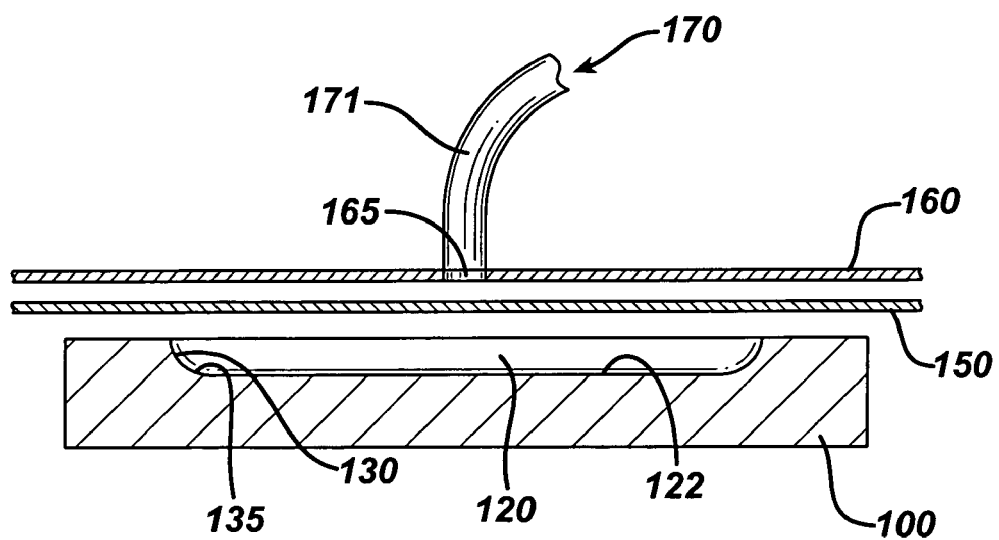
FIG. 5 is a schematic of a molding apparatus useful to mold a cavity in the bottom sheet.

In the process of the present invention as illustrated in FIG. 5, a mold 100 as seen in FIG. 3A is used. Mold 100, as illustrated in FIG. 3A, is seen to be configured to produce a two package strip in that it has side-by-side cavities 120. The cavities 120 are seen to have bottoms 122 and open tops 125 and a depth. Cavities 120 are seen to have substantially curved or arcuate peripheries at any horizontal cross-section (i.e., at any horizontal plane) along the depth of the cavity. For example, a periphery having curved sides 130 connected with rounded corners 135. The amount of curvature of the periphery including the sides is sufficient to effectively provide for flat molded bottom sheets that can be readily assembled and sealed to flat planar top laminate sheets. For example, the curvature may range from 0.25" to 9", although not limited thereto. The relative degree of curvature can be smaller/large depending on the overall size and configuration of the cavity being formed. Those skilled in this art will appreciate that the parameters will vary depending on adjacent geometries and overall size of the cavity. Tangency from one arc to the next is recommended. A radius from the top surface of the mold to the sidewall of the mold cavity is preferred to reduce the number of pinholes created during the foil forming process. Substantially curved or arcuate is defined to mean that any segment of the periphery will be curved or arcuate with substantially no linear sections, however, it can be appreciated that there may be a small section of a segment that is linear and which may provide the benefits of the present invention. The segments may have different radii of curvature and the degree of curvature may range from slight (for example sides) to significant (for example, corners).

Figure 2B:
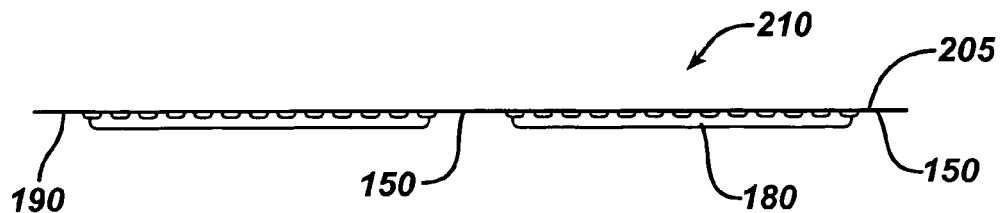
FIG. 2B is a side view of the package of FIG. 2A, illustrating the molded bottom.
Figure 3B:
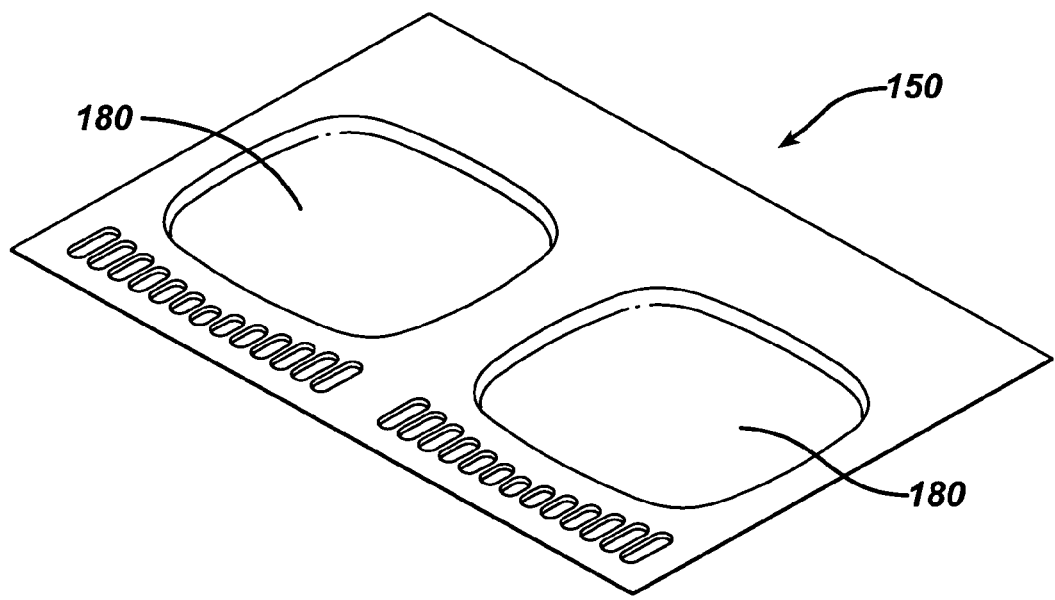
FIG. 3B is a perspective view of a bottom sheet molded using the mold of FIG. 3A, and having a package cavity wherein the package cavity has a curved periphery.

Again referring to FIG. 5, a first bottom laminate sheet 150 is placed on top of the mold 100. A flat top platen 160 engages the laminate sheet 150 against the mold 100. A burst of compressed air 170 in tube 171 is directed through opening 165 against sheet 150 causing the section of foil laminate 150 on top of the mold 100 to deform downwardly into mold cavities 120, thereby taking the shape of mold cavities 120 and forming package cavities 180 in the sheet 150. Referring to FIGS. 2A and 2B, each package cavity 180 has curved or arcuate side walls 182, and curved or rounded corners 185 forming a curved or arcuate periphery at any horizontal section along the depth of package cavity 180. Surrounding the cavities 180 is the flat flange section 190. The molded first laminate 150 is also illustrated in FIG. 3B. Then a product to be packaged such as a conventional surgical suture package (not shown) is inserted in each cavity 180, and a second flat, top laminate sheet 205 is sealed in a conventional manner to laminate 150, for example by heat sealing to form the sealed intermediary package 210 having bio-barrier vent 220. After sterilization (e.g., preferably gaseous such as ethylene oxide) the individual packages have the connection to the gas vent sealed, and the vent 220 is cut away and the packages are separated from each other by cutting.

Figure 4B:
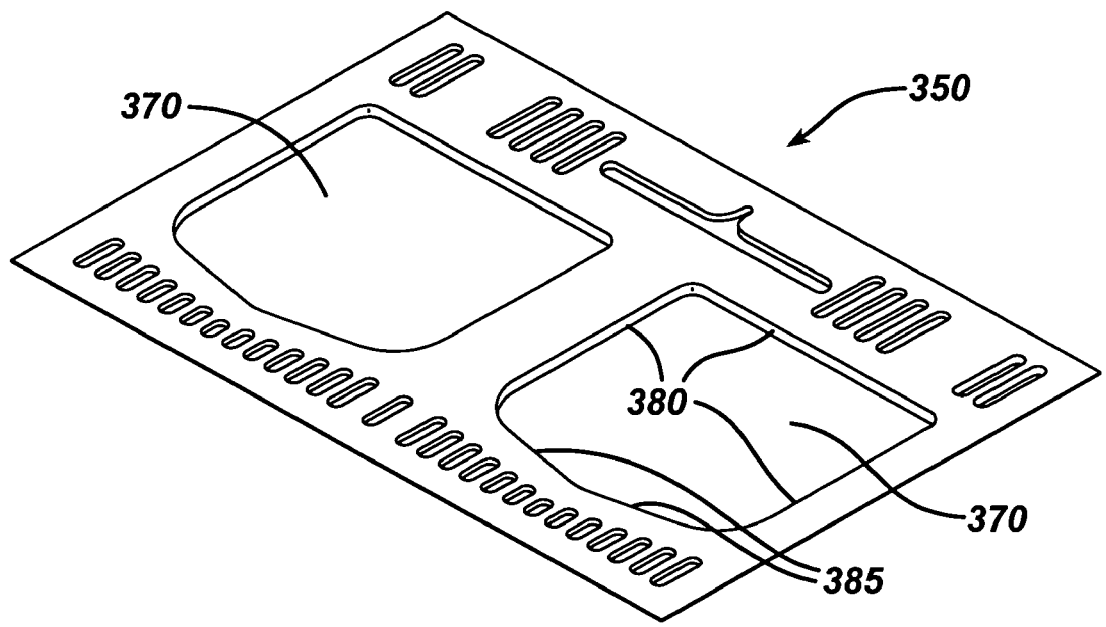
FIG. 4B is a perspective view of a bottom sheet molded using the prior art mold of FIG. 4A, having a package cavity, wherein the package cavity has a periphery with linear segments.

A mold 300 of the prior art is illustrated in FIG. 4a, and a bottom foil laminate 350 molded in mold 300 is seen in FIG. 4B. The mold 300 is seen to have mold cavities 320 having peripheries with three substantially straight sides 330 connected to angulated straight sides 335. The bottom molded foil laminate 350 is similarly seen to have package cavity 370 having package cavities with three substantially straight sides 380 connected to angulated straight sides 385.

Figure 6:
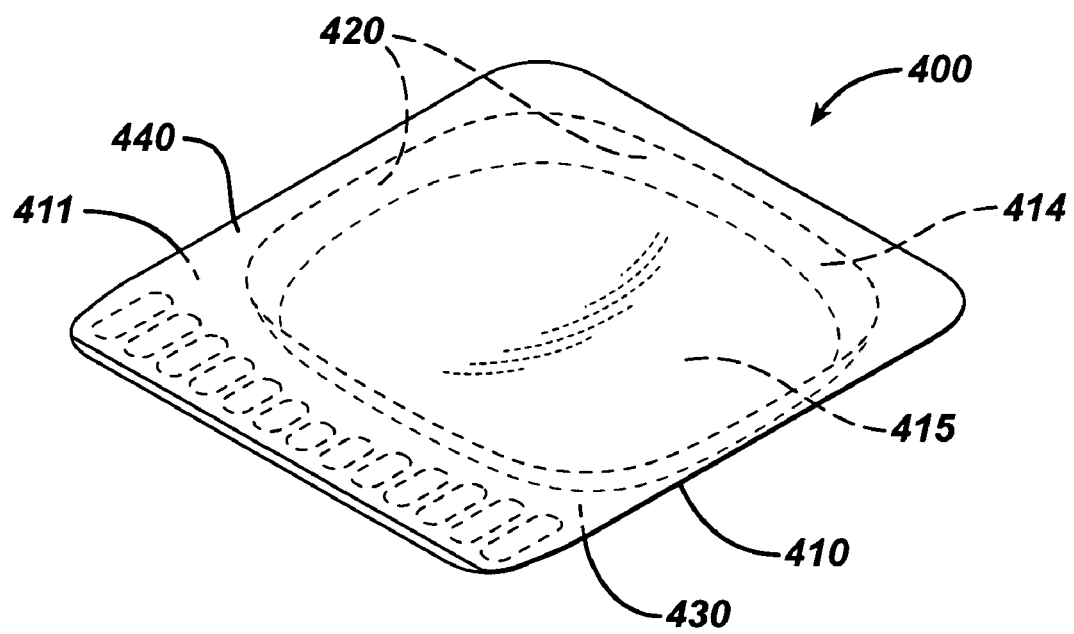
FIG. 6 is a perspective view of an alternate configuration of a foil package having a substantially rounded package cavity with an arcuate periphery made using the process of the present invention.

An alternative embodiment of a package manufactured by the process of the present invention is illustrated in FIG. 6. Package 400 is seen to have molded bottom laminate foil 410 having package cavity 415 surrounded by arcuate sides 420 making up the arcuate or curved periphery 414 of the package cavity 415. The foil 410 has bottom 430. Sealed to the top 411 of bottom laminate foil 410 is the top laminate foil member 440. The package cavity 415 is seen to be deeper than the package cavity 180 of package 200 and to have a substantially rounded bottom configuration rather than having a flat bottom.

The novel process of the present invention for forming cavities in foil stock has many advantages. One advantage of the anti-curling process is that the material lays flat. The flatness of the foil allows for easier material handling both in a manual and automated sealing process. The flatness also aids in placement of product within the formed cavity. Bent foil is harder to handle, usually requiring manual flattening, and is more difficult to place product in. Occasionally bent foil leads to problem with seal quality, wherein a channel within the sealed area can possibly form, depending on the amount of bending. Another advantage is the economy in manufacturing gained by improving the efficiency of the sealing process.

Although this invention has been shown and described with respect to detailed embodiments thereof, it will be understood by those skilled in the art that various changes in form and detail thereof may be made without departing from the spirit and scope of the claimed invention.

We claim:

1. An anti-curling process for manufacturing foil packages from laminated foil sheets, comprising:

providing a planar, pre-cut metal foil laminate top sheet and an opposed, pre-cut metal foil laminate bottom sheet, each pre-cut metal foil laminate sheet comprising a top polymeric sheet, an inner metal foil sheet, and a bottom polymeric sheet;

orienting the sheets such that the bottom polymeric sheets of the metal foil laminates are opposed and facing each other;

providing a mold having a mold cavity, said mold cavity having a periphery and a depth, wherein the periphery is substantially curved at any horizontal cross-section along the depth of the mold cavity;

forming a package cavity in the bottom metal foil laminate sheet using the mold such that the package cavity has a periphery and a depth, said package cavity surrounded by walls and a bottom, wherein the periphery is substantially curved at any horizontal cross-section along the depth of the cavity, and wherein there is an outwardly extending flange member about the periphery of the cavity after the forming; and, mounting the top sheet to the bottom sheet such that the package cavity in the bottom sheet is enclosed, wherein after the forming of the package cavity the outwardly extending flange member of the bottom sheet is substantially uncurled.

2. The process of claim 1, wherein a surgical suture and needle are inserted into the cavity.

3. The process of claim 2, wherein the surgical suture and needle are in a dispenser package.

4. The process of claim 1, wherein the mold and the bottom metal foil laminate sheet have cavities comprising peripheries that are curved at any horizontal cross-section.

5. The process of claim 1, wherein the metal foil laminate comprises aluminum.

6. The process of claim 1, wherein the polymeric sheet of the metal foil laminate comprises PET.

7. The process of claim 1, wherein the peripheries of the mold cavity and the package cavity comprise joined segments, wherein at least two of the segments have a different radius of curvature.

8. The process of claim 1, wherein the bottom of the package cavity is flat.

9. The process of claim 1, wherein the bottom of the package cavity is rounded.

* * * * *